United States Patent

Blom

Patent Number: 5,957,978
Date of Patent: Sep. 28, 1999

[54] VALVED FENESTRATED TRACHEOTOMY TUBE

[75] Inventor: Eric D. Blom, Carmel, Ind.

[73] Assignee: Hansa Medical Products, Inc., Indianapolis, Ind.

[21] Appl. No.: 08/996,282

[22] Filed: Dec. 22, 1997

[51] Int. Cl.[6] .................................................. A61M 16/00
[52] U.S. Cl. .................. 623/9; 128/200.26; 128/207.14; 128/207.12
[58] Field of Search .................................. 623/9; 381/70; 128/207.12, 207.17, 205.24, 206.15

[56] References Cited

U.S. PATENT DOCUMENTS

| 4,596,248 | 6/1986 | Lieberman | 128/207.16 |
|---|---|---|---|
| 5,255,676 | 10/1993 | Russo | 128/207.14 |
| 5,329,921 | 7/1994 | Socaris et al. | 128/207.14 |
| 5,339,808 | 8/1994 | Don Michael | 128/207.15 |
| 5,343,857 | 9/1994 | Schneider et al. | 128/207.14 |
| 5,349,950 | 9/1994 | Ulrich et al. | 128/207.16 |
| 5,391,205 | 2/1995 | Knight | 623/9 |
| 5,392,775 | 2/1995 | Adkins, Jr. et al. | 128/207.16 |
| 5,515,844 | 5/1996 | Christopher | 128/200.26 |
| 5,584,288 | 12/1996 | Baldwin | 128/202.28 |
| 5,599,333 | 2/1997 | Atkinson | 604/326 |
| 5,687,767 | 11/1997 | Bowers | 128/206.15 |
| 5,688,256 | 11/1997 | Surrat et al. | 604/355 |
| 5,746,199 | 5/1998 | Bayron et al. | 128/205.24 |

OTHER PUBLICATIONS

Tracheostomy and Laryngectomy Tubes, pp. 568 and 572.
Tracheostomy Tube Adult Home Car Guide, Shiley Tracheostomy Products, Mallinckrodt Medical, pp. 1–40.

Primary Examiner—David H. Willse
Assistant Examiner—Suzette J. Jackson
Attorney, Agent, or Firm—Barnes & Thornburg

[57] ABSTRACT

A tracheotomy tube comprises a first port for orienting outside the neck of a wearer, a second port for orienting within the trachea of the wearer, and a passageway connecting the first and second ports to permit the flow of gases from the first port to the second port on inhalation by the wearer and from the second port to the first port on exhalation by the wearer. The tracheotomy tube further comprises a third port oriented between the first and second ports, and a valve controlling flow through the third port. The valve opens to permit flow from the passageway through the third port.

8 Claims, 3 Drawing Sheets

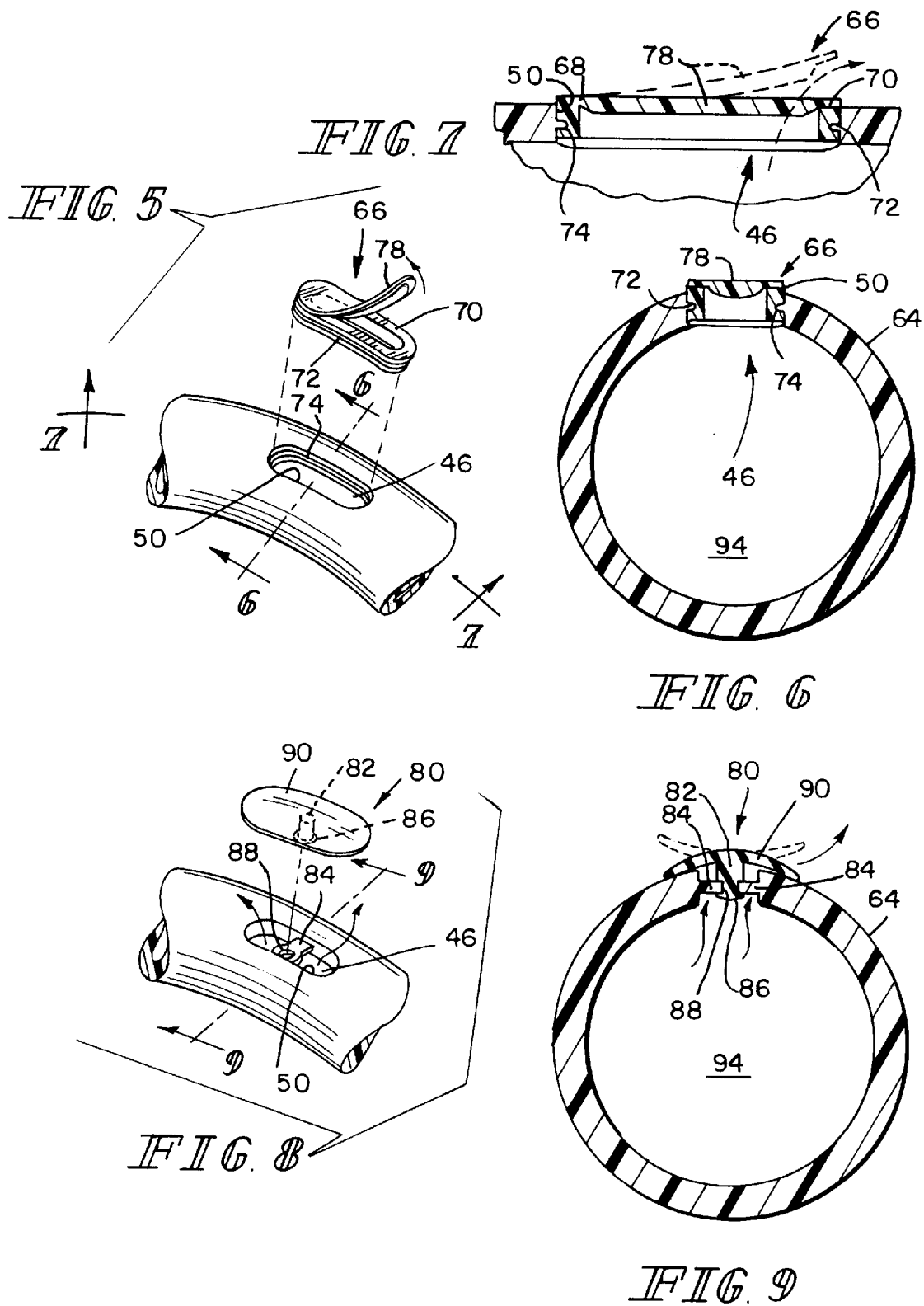

VALVED FENESTRATED TRACHEOTOMY TUBE

This invention relates to improvements in tracheotomy tubes.

Various types of tracheotomy tubes are known. Such tubes are available in a number of different materials and designs. Tracheotomy tubes of metal, for example, Tucker metal tracheotomy tubes, are available from, for example, Pilling Weck Incorporated. Tracheotomy tubes constructed from various types of resins, silicones and the like are available from, for example, Shiley Incorporated.

According to the invention, a tracheotomy tube comprises a first port for orienting outside the neck of a wearer, a second port for orienting within the trachea of the wearer, and a passageway connecting the first and second ports to permit the flow of gases from the first port to the second port on inhalation by the wearer and from the second port to the first port on exhalation by the wearer. The tracheotomy tube further comprises a third port oriented between the first and second ports, and a valve controlling flow through the third port. The valve opens to permit flow from the passageway through the third port.

According to an illustrative embodiment, the valve comprises a flexible membrane having a slit in it. The slit controls flow through the third port.

According to another illustrative embodiment, the valve comprises a flap for covering the third port and a hinge for connecting the flap to the tracheotomy tube.

According to yet another illustrative embodiment, the valve comprises a flexible member for covering the third port. The flexible member and the tracheotomy tube include complementary first and second attachment members, respectively, for attaching the flexible member to the tracheotomy tube. The second attachment member provides an attachment point located within the third port for attachment of the first attachment member to the second attachment member at the attachment point.

According to illustrative embodiments, the tracheotomy tube further comprises an inflatable cuff between the second and third ports, and a second passageway for introducing an inflating fluid into the cuff. The cuff can be inflated in situ in the trachea of the wearer to impede the flow of fluids between the cuff and the trachea when the cuff is inflated.

The invention may best be understood by referring to the following detailed description and accompanying drawings which illustrate the invention. In the drawings:

FIG. 5 illustrates a fragmentary exploded perspective view of another device constructed according to the invention;

FIG. 6 illustrates a fragmentary sectional view of the device illustrated in FIG. 5, taken generally along section lines 6—6 of FIG. 5;

FIG. 7 illustrates a fragmentary sectional view of the device illustrated in FIGS. 5–6, taken generally along section lines 7—7 of FIGS. 5–6;

FIG. 8 illustrates a fragmentary exploded perspective view of another device constructed according to the invention;

FIG. 9 illustrates a fragmentary sectional view of the device illustrated in FIG. 8, taken generally along section lines 9—9 of FIG. 8; and, FIG. 10 illustrates a fragmentary sectional view of another device constructed according to the invention.

Figure 1:
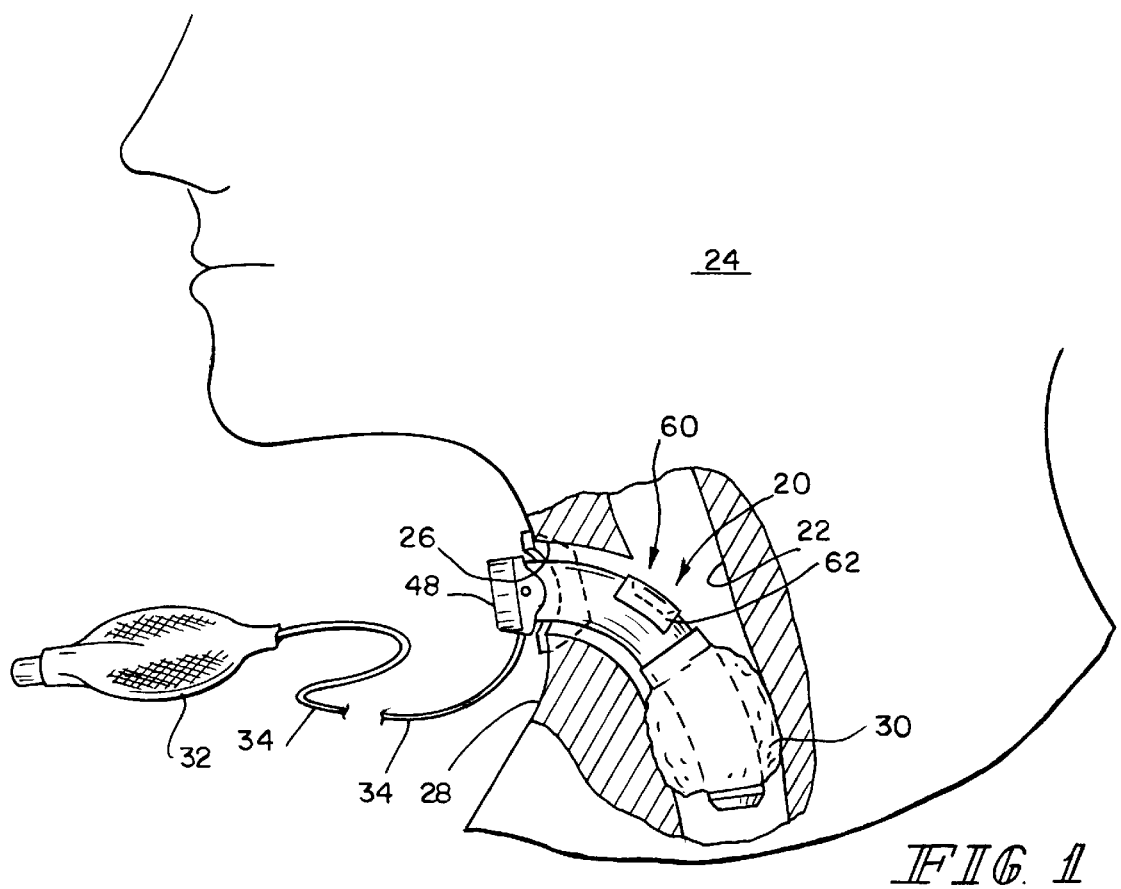
FIG. 1 illustrates a fragmentary side elevational view of a device constructed according to the invention oriented in the trachea of a wearer.
Figure 3:
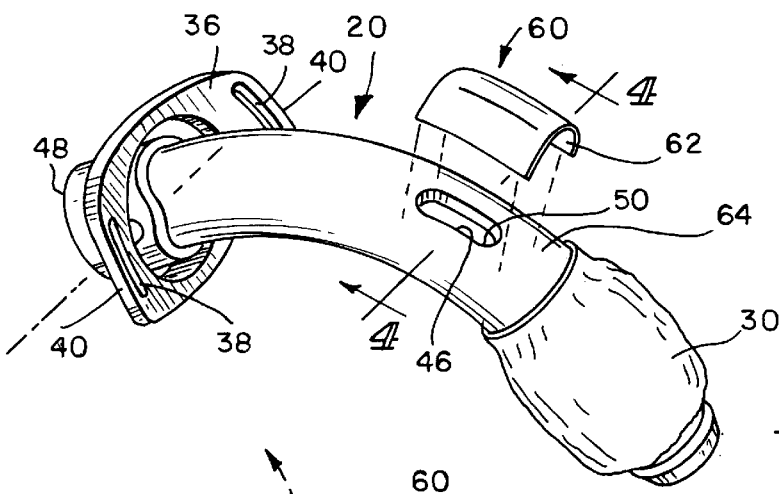
FIG. 3 illustrates a partly exploded perspective view of the device illustrated in FIG. 1.
Figure 4:
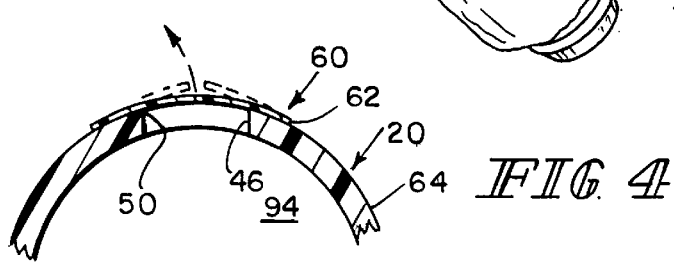
FIG. 4 illustrates a fragmentary sectional view of the device illustrated in FIGS. 1–2, taken generally along section lines 3—3 of FIGS. 1–2.
Figure 2:
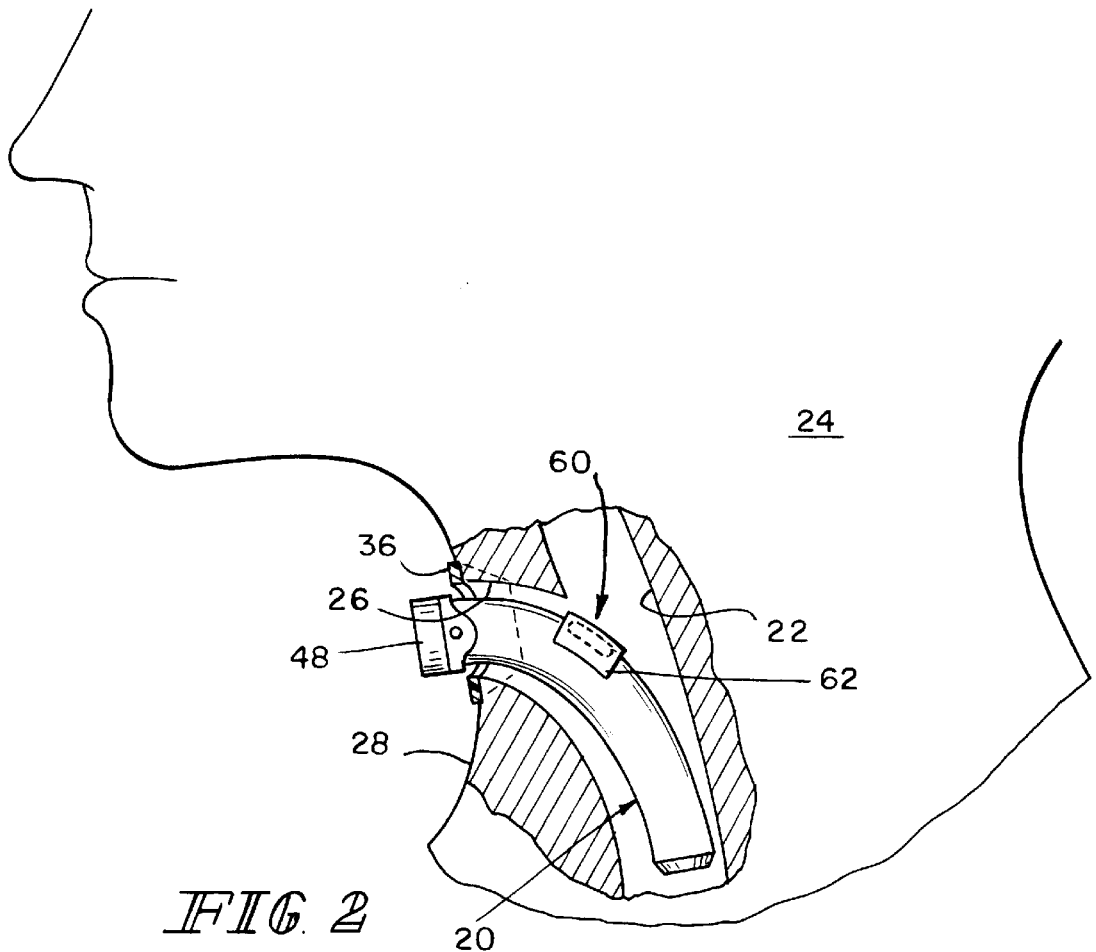
FIG. 2 illustrates a fragmentary side elevational view of another device constructed according to the invention oriented in the trachea of a wearer.

Valved tracheotomy tubes 20 (also frequently referred to as outer cannulae) constructed according to the invention are illustrated in FIGS. 1–2 installed in the trachea 22 of a wearer 24. A tracheostoma 26 formed in the front of the wearer 24's neck 28 provides an airway into the trachea 22 entering below the wearer 24's larynx. Tracheotomy tubes are typically available in cuffed (FIG. 1) or cuffless (FIG. 2) varieties. Tube 20 illustrated in FIG. 1 has a cuff 30 and a reservoir 32 for indicating when the cuff 30 is inflated, and connecting conduit 34 for inflating the cuff 30 to seal the cuff 30 against the wall of the wearer's trachea 22. Cuffs such as cuff 30 are useful in a number of different situations, for example, to prevent material which enters the trachea 22 above cuff 30 from getting into the wearer 24's lungs, and to prevent leakage of gases upward past cuff 30 for a wearer on a ventilator. Tracheotomy tubes typically also are provided with some type of mechanism for attachment of the tracheotomy tube to the neck of a wearer. For example, and with reference to FIGS. 1–2, the illustrated tracheotomy tube 20 includes a pivotally mounted front plate 36 having a slot 38 adjacent each of its sides 40 to permit attachment of a belt or strap to the sides 40 of front plate 36 and passage of the belt or strap around the neck 28 of the wearer 24.

Where a cuffed tracheotomy tube 20 is worn, a mechanism must be provided for the passage of exhaled gases from the wearer 24's lungs upward past the cuff 30 and out of the tracheotomy tube 20 so that speech may be produced. One way that this has been done is by the provisions of fenestrations 46 above the cuff 30. Exhaled gases flowing upward through the tracheotomy tube 20 can be channeled through the fenestrations 46 by the wearer 24 occluding the port 48 of the tube 20, for example, with a fingertip.

One problem which has been encountered with fenestrated tracheotomy tubes is that the tissue of the trachea 22 adjacent the fenestrations 46 can be irritated by the edges 50 of the fenestrations 46. It must be remembered that the trachea 22 and the tracheotomy tube 20 move relative to each other. The amount of this relative movement may be relatively small, or it may be considerable, depending on the particular wearer 24's circumstances. For example, if the wearer 24 is on a ventilator, there will typically be considerable relative movement between the tracheotomy tube 20 and the wearer's trachea 22. The contact between the edges 50 of the fenestrations 46 and the tissue of the wearer 24's trachea 22 frequently causes direct irritation of the wearer 24's trachea 22 or the formation of so-called granulation tissue. The granulation tissue frequently forms into the fenestrations 46. The presence of granulation tissue in the lumen of the tracheotomy tube 20 can block passage of airflow for speech and respiration through the fenestrations 46, can create difficulty for the wearer and others, such as health care providers, in removal of the tracheotomy tube 20 and insertion of a new tracheotomy tube 20, and can create difficulty in the removal and reinsertion of an inner cannula which typically resides within the tracheotomy tube 20. Of course, it would be helpful to reduce this distress to the wearer 24. Immediate improvement would be available if granulation tissue were greatly reduced or eliminated.

According to the invention, the fenestration 46 is closed by a valve which is opened by the wearer 24, for example, by occluding the port 48, for example, whenever the wearer 24 wishes to speak. The valve is made sufficiently sensitive that it readily opens under the pressure the wearer 24 typically exerts when the wearer 24 wishes to speak, and closes whenever the pressure drops below that required for speech as the wearer 24 removes his or her finger from port 48 and reestablishes airflow between the wearer 24's lungs and port 48. The valve 60 illustrated in FIGS. 1–4 is a slit type valve provided in a membrane 62 of, for example, silicone sheeting. Membrane 62 is attached by any suitable means, such as an appropriate adhesive, to the outer sidewall 64 of tracheotomy tube 20 around fenestration 46. Speech pressure on valve 60 from inside tracheotomy tube 20 opens valve 60, permitting exhaled gases to flow upward through the trachea 22 for the creation of speech.

In another embodiment 66 of the valve illustrated in FIGS. 5–7, the valve 66 is a flap type valve attached by a so-called living hinge 68 to its own valve seat 70. The entire valve 66 including the valve flap, the valve seat and the hinge by which the flap is attached to the seat is formed together, for example, from a molded silicone or the like, and is inserted in assembled configuration into the fenestration 46. The illustrated valve 66 is provided with a circumferential groove 72 and the edge 50 of the fenestration 46 with a complementary bead 74 for engaging the groove 72 to aid in the retention of the valve 66 in the tube 20. Of course, this attachment mechanism can be supplemented by a suitable adhesive or the like. The flap 78 of valve 66 assumes the position illustrated in broken lines in FIG. 7 to permit the flow of gases through fenestration 46 and the formation of speech whenever the user occludes port 48. See FIGS. 1–2.

In another embodiment of the valve illustrated in FIGS. 8–9, the valve 80 is a so-called umbrella type valve attached by a stem 82 to a support 84 which extends across the fenestration 46. The stem 82 is formed with a head 86 which is captured in a hole 88 provided for this purpose in support 84. The umbrella 90 of valve 80 assumes the position illustrated in broken lines in FIG. 9 to permit the flow of gases through fenestration 46 and the formation of speech whenever the user occludes port 48. The umbrella 90 and stem 82 illustratively can be molded as a single component from silicone or the like.

Figure 10:
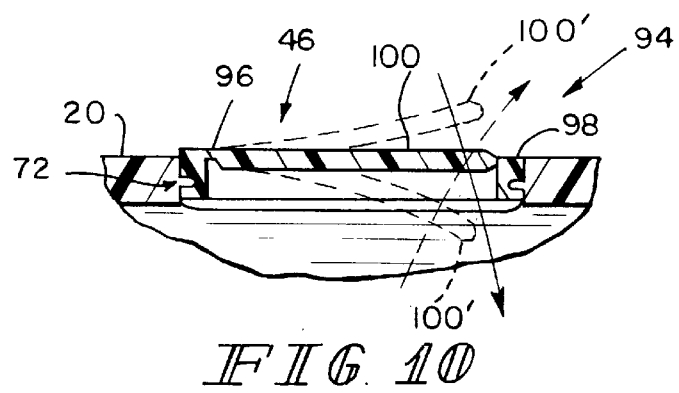

In another embodiment of the valve illustrated in FIG. 10, the valve 94 is a flap type valve attached by a living hinge 96 to its own perimetral support 98. The entire valve 94 including the valve flap, the hinge and the perimetral support 98 is formed together, for example, from a molded silicone or the like, and is inserted in assembled configuration into the fenestration 46. The illustrated valve 94 is provided with a circumferential groove 72 and the edge 50 of the fenestration 46 with a complementary bead 74 for engaging the groove 72 to aid in the retention of the valve 94 in the tube 20. Again, this attachment mechanism can be supplemented by a suitable adhesive or the like. The flap 100 of valve 94 assumes the position 100' illustrated in broken lines in FIG. 10 to permit the flow of gases through fenestration 46 out of tube 20 into the trachea 22 of the wearer 24, and assumes the position 100" illustrated in broken lines in FIG. 10 to permit the flow of gases through fenestration 46 into tube 20 from the trachea 22 of the wearer 24.

It will be appreciated from the drawings that the valves 60, 66, 80 all lie virtually flat against the outer side of the wall 64 of the tracheotomy tube 20 or are recessed within the wall 64. This further reduces the likelihood of irritation of the tissue of the trachea 22 of the wearer 24. It will also be appreciated from the drawings that the valves 60, 66, 80 provide essentially no obstruction to the passage of, for example, the inner cannula or other medical instruments, through the lumen of the tracheotomy tube 20. This facilitates inserting and removing the inner cannula or such other medical instruments and the like through the lumen during treatment of the wearer 24, and reduces the likelihood of damage to the valve 60, 66, 80 caused by such insertion and removal.

What is claimed is:

1. A tracheotomy tube comprising an inner surface and an outer surface, a first port for orienting outside the neck of a wearer, a second port for orienting within the trachea of the wearer, the inner surface defining a passageway connecting the first and second ports to permit the flow of gases from the first port to the second on inhalation by the wearer and from the second port to the first on exhalation by the wearer, a third port between the first and second ports, and a valve for controlling flow through the third port, the third port connecting the inner and outer surfaces to thereby permit exhaled gases to flow from said tube into the trachea.

2. The tracheotomy tube of claim 1 further comprising an inflatable cuff between the second and third ports and second passageway for introducing an inflating fluid into the cuff in situ in the trachea of the wearer to impede the flow of fluids between the cuff and the trachea when the cuff is inflated.

3. The tracheotomy tube of claim 1 wherein the valve comprises a flexible membrane having a slit in it.

4. The tracheotomy tube of claim 3 further comprising an inflatable cuff between the second and third ports and second passageway for introducing an inflating fluid into the cuff in situ in the trachea of the wearer to impede the flow of fluids between the cuff and the trachea when the cuff is inflated.

5. The tracheotomy tube of claim 1 wherein the valve comprises a flap for covering the third port and a hinge for connecting the flap to the tracheotomy tube.

6. The tracheotomy tube of claim 5 further comprising an inflatable cuff between the second and third ports and second passageway for introducing an inflating fluid into the cuff in situ in the trachea of the wearer to impede the flow of fluids between the cuff and the trachea when the cuff is inflated.

7. The tracheotomy tube of claim 1 wherein the valve comprises a flexible member for covering the third port, the flexible member including a first attachment member and the tracheotomy tube including a second attachment member, the first and second attachment members cooperating to attach the flexible member to the tracheotomy tube, the second attachment member providing an attachment point located within the third port for attachment of the first attachment member to the second attachment member at the attachment point.

8. The tracheotomy tube of claim 7 further comprising an inflatable cuff between the second and third ports and second passageway for introducing an inflating fluid into the cuff in situ in the trachea of the wearer to impede the flow of fluids between the cuff and the trachea when the cuff is inflated.

* * * * *